United States Patent
Davis et al.

(10) Patent No.: US 8,009,938 B2
(45) Date of Patent: Aug. 30, 2011

(54) ADVANCED PROCESS SENSING AND CONTROL USING NEAR INFRARED SPECTRAL REFLECTOMETRY

(75) Inventors: Matthew Fenton Davis, Felton, CA (US); Lei Lian, Santa Clara, CA (US)

(73) Assignee: Applied Materials, Inc., Santa Clara, CA (US)

( * ) Notice: Subject to any disclaimer, the term of this patent is extended or adjusted under 35 U.S.C. 154(b) by 853 days.

(21) Appl. No.: 12/040,698

(22) Filed: Feb. 29, 2008

(65) Prior Publication Data
US 2009/0218314 A1 Sep. 3, 2009

(51) Int. Cl.
G02B 6/00 (2006.01)
G02B 6/04 (2006.01)
C23F 1/00 (2006.01)
G01J 3/45 (2006.01)
C03B 37/023 (2006.01)

(52) U.S. Cl. ....... 385/12; 385/115; 216/60; 156/345.24; 356/451; 65/385; 65/469

(58) Field of Classification Search .................. 385/115, 385/116, 141, 14, 15, 16, 12; 65/385, 469; 356/451; 156/345.33, 345.24; 216/60
See application file for complete search history.

(56) References Cited

U.S. PATENT DOCUMENTS

| | | | |
|---|---|---|---|
| 5,180,464 A | 1/1993 | Tatsumi et al. | 156/626 |
| 5,499,733 A | 3/1996 | Litvak | 216/38 |
| 6,081,334 A | 6/2000 | Grimbergen et al. | 356/357 |
| 6,413,873 B1 | 7/2002 | Li et al. | 438/711 |
| 6,745,095 B1 * | 6/2004 | Ben-Dov et al. | 700/121 |
| 7,330,244 B2 | 2/2008 | Davis et al. | 356/72 |
| 7,712,434 B2 * | 5/2010 | Dhindsa et al. | 118/723 E |
| 2004/0018647 A1 | 1/2004 | Jones et al. | 438/8 |
| 2004/0203177 A1 | 10/2004 | Davis et al. | 438/14 |
| 2006/0012796 A1 | 1/2006 | Saito et al. | 356/451 |
| 2007/0039548 A1 | 2/2007 | Johnson | 118/665 |
| 2007/0256785 A1 | 11/2007 | Pamarthy et al. | 156/345.33 |
| 2009/0218314 A1 * | 9/2009 | Davis et al. | 216/60 |
| 2010/0099266 A1 * | 4/2010 | Oswald et al. | 438/719 |

FOREIGN PATENT DOCUMENTS

| | | |
|---|---|---|
| EP | 0898300 A2 | 2/1999 |
| JP | 404150025 A | 5/1992 |
| KR | 20030000274 A | 1/2003 |
| RU | 2036418 | 5/1995 |
| WO | 0034984 A2 | 6/2000 |
| WO | 03041123 A2 | 5/2003 |

OTHER PUBLICATIONS

Sylvie Bosch-Charpenay et al.,"Real-Time Etch-Depth Measurements of MEMS Devices," Journal of Microelectromechanical Systems, Apr. 2002 vol. 11(2): pp. 111-117. Charles W. Cullen et al., "Temperature Measurement of Metal-Coated Silicon Wafers by Double-Pass Infrared Transmission," IEEE Transactions on Semiconductor Manufacturing, Aug. 1995 vol. 8(3): pp. 346-351.
PCT International Search Report and Written Opinion dated Aug. 19, 2009.

* cited by examiner

Primary Examiner — Brian Healy
(74) Attorney, Agent, or Firm — Patterson & Sheridan, L.L.P.

(57) ABSTRACT

Embodiments described herein provide a method and apparatus for obtaining process information in a substrate manufacturing process using plasma. In one embodiment, a chamber is provided having one or more optical metrology modules that are positioned such that optical energy from the plasma process is detected at substantially orthogonal angles. Metrics derived from detected optical energy may be used for endpoint determination, substrate temperature, and monitoring of critical dimensions on the substrate.

24 Claims, 13 Drawing Sheets

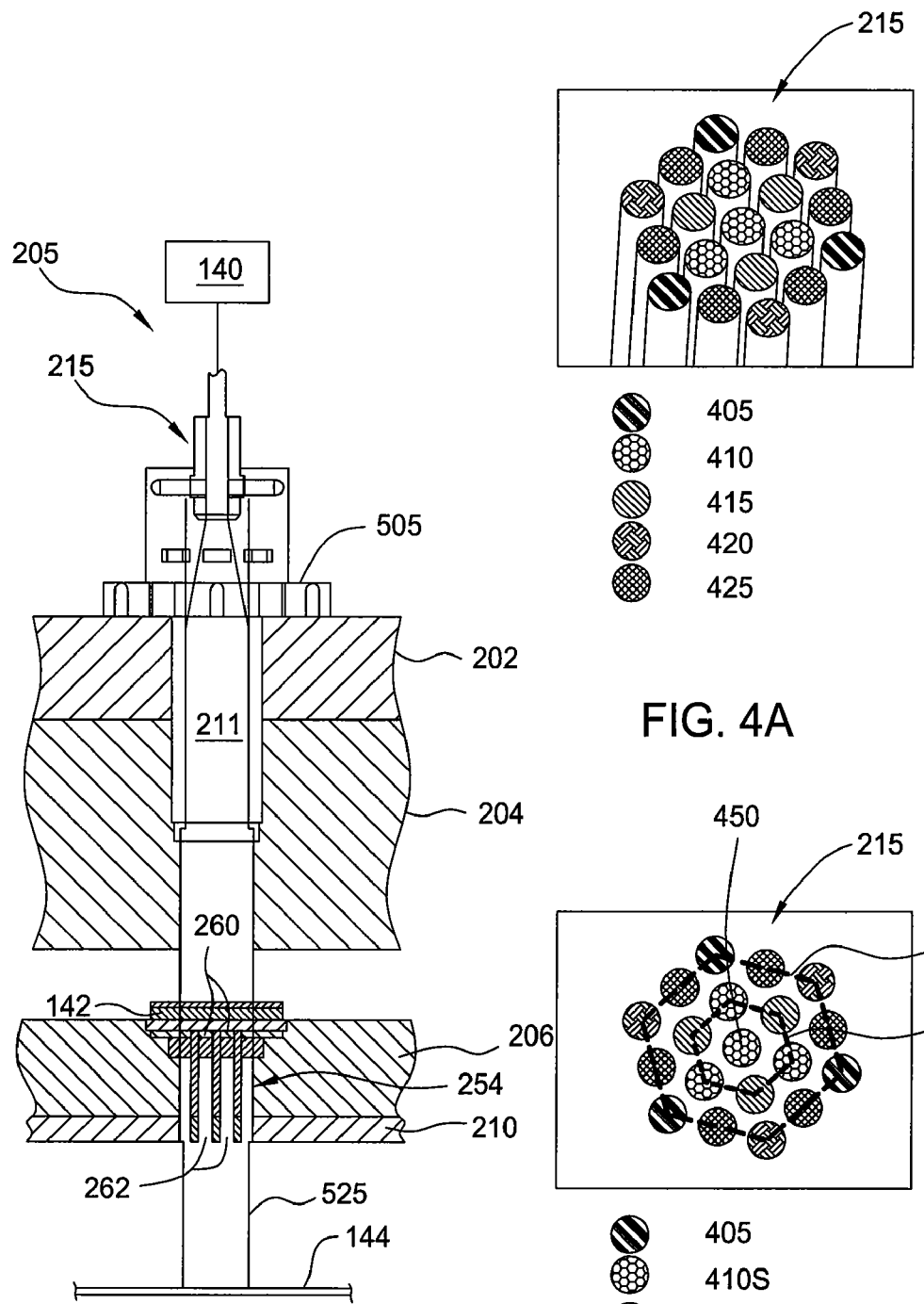
FIG. 5
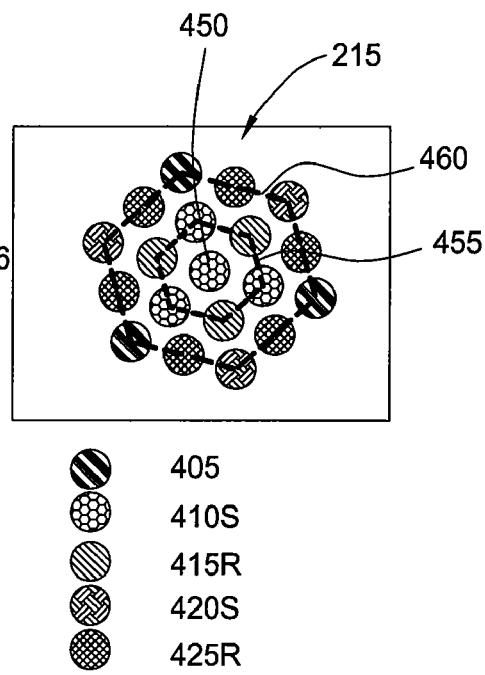
FIG. 4A
FIG. 4B

ADVANCED PROCESS SENSING AND CONTROL USING NEAR INFRARED SPECTRAL REFLECTOMETRY

BACKGROUND

1. Field

Embodiments of the invention generally relate to processes for fabricating electronic devices on substrates, and more specifically, to monitoring process parameters in an electronic device fabrication process.

2. Description of the Related Art

The demand for faster, more powerful integrated circuit (IC) devices has introduced new challenges for IC fabrication technology, including the need to etch high aspect ratio of features such as trenches or vias on a substrate, such as a semiconductor wafer. For example, deep trench storage structures used in some dynamic random access memory applications require deep high aspect ratio trenches etched into a semiconductor substrate. Deep silicone trench etching is typically carried out in a reactive ion etching (RIE) process utilizing a silicon oxide mask.

Conventional systems which have shown robust performance in etching high aspect ratio features in semiconductor wafers is the APPLIED CENTURA HART™ Etch System and the Decoupled Plasma Source (DPS®) system available from Applied Materials, Inc. located in Santa Clara, Calif. The HART™ etching system utilizes a MERIE reactor capable of etching trenches having aspect ratios up to 70:1 while maintaining trench depth uniformity of 5 percent from center to edge. However, in order to enable fabrication of integrated circuits having sub-90 nm critical dimensions, circuit designers have demanded improved trench uniformity at even higher aspect ratios. Thus, it would be desirable to improve etching performance to enable the realization of next generation devices.

In order to meet these challenges, improvements must be made in monitoring process parameters on the wafer, such as wafer temperature and feature depths or dimensions, during processing. Generally, conventional measurement techniques and devices include thermocouples or probes positioned in proximity to the wafer, such as pyrometers or other probes to monitor wafer temperature. Other conventional measurement techniques include scatterometry, optical emission spectroscopy, laser inferometry, and the like, or a conventional determination in the time domain and/or frequency domain to facilitate an endpoint for an etch process. While these conventional processes may, in some instances, provide useful results, the ever-increasing trench depths, aspect ratios, and critical dimensions may leave the conventional measurement processes lacking for next generation processes.

Therefore, there is a need for an improved apparatus and method for providing an accurate and real-time metric of processing parameters.

SUMMARY

Embodiments described herein provide a method and apparatus for obtaining process information in a substrate manufacturing process using plasma.

In one embodiment, a processing chamber is described. The processing chamber includes a chamber body assembly having a processing volume, a showerhead assembly coupled to a ceiling of the chamber body and having a region transmissive to an optical metrology signal, an optical monitoring device arranged to view the processing volume at a radial position of the chamber body, and a spectral sensing system arranged to view the processing volume of the chamber body through the transmissive region of the showerhead assembly at an angle orthogonal to the plane of the showerhead.

In another embodiment, a fiber optic cable bundle coupled to a radiation source and a spectrometer is described. The fiber optic cable includes a first portion comprising at least one source fiber, a second portion comprising a plurality of first source fibers and a plurality of first signal fibers in communication with the radiation source, wherein a portion of the plurality of first source fibers are arranged in a spaced-apart relationship relative to the plurality of first signal fibers, and a third portion comprising a plurality of second source fibers, a plurality of second signal fibers, and a plurality of inactive fibers.

In another embodiment, a method for processing a substrate is described. The method includes etching a substrate positioned on a substrate support disposed in an etch chamber, the substrate etched through a patterned masking layer in the presence of a plasma, introducing optical energy into the plasma and directed towards the substrate, collecting a first signal and a second signal from the plasma, routing the first signal through a fiber optic bundle to a detector, and controlling the etch process in response to the collected signals.

In another embodiment, a fiber optic cable bundle coupled to a radiation source and at least one spectrometer is described. The fiber optic cable bundle includes a plurality of optical fibers secured in a bundle, the bundle comprising a first portion comprising at least one source fiber having a first end coupled to the radiation source and a second end positioned to direct radiation from the source into a processing chamber, a second portion comprising a plurality of first return fibers having a first end in communication with the at least one spectrometer and a second end positioned to receive optical signals originating the processing chamber, and a third portion comprising a plurality of inactive fibers, wherein the second portion and the third portion are arranged on a common radius, and each source fiber is separated along the common radius by either at least one of the return fibers, at least one of the inactive fibers, or both return and inactive fibers.

In another embodiment, a method for processing a substrate is described. The method includes etching a substrate positioned on a substrate support disposed in an etch chamber, the substrate etched through a patterned masking layer in the presence of a plasma, introducing optical energy into the plasma and directed towards the substrate, collecting a first signal and a second signal from the plasma, routing the first signal through a fiber optic bundle to a detector, wherein the fiber optic cable bundle comprises a first portion comprising at least one source fiber having a first end coupled to a radiation source and a second end positioned to direct radiation from the source into a processing chamber, a second portion comprising a plurality of first return fibers having a first end in communication with at least one spectrometer and a second end positioned to receive optical signals originating the processing chamber, and a third portion comprising a plurality of inactive fibers, wherein the second portion and the third portion are arranged on a common radius, and each source fiber is separated along the common radius by either at least one of the return fibers, at least one of the inactive fibers, or both return and inactive fibers, and controlling the etch process in response to the collected signals.

In another embodiment, a computer-readable medium is provided to control an etch process. In one embodiment computer-readable medium contains instructions, that when executed by a processing system, control an etch process performed in the processing system, the etch process comprising, etching a substrate positioned on a substrate support disposed in a processing system, the substrate etched through a patterned masking layer in the presence of a plasma, directing optical energy through the plasma towards the substrate, collecting a first signal and a second signal from the plasma, routing the first signal through a fiber optic bundle to a detector, and controlling the etch process in response to the collected signals. The fiber optic cable bundle includes a first portion comprising at least one source fiber having a first end coupled to a radiation source and a second end positioned to direct radiation from the source into a processing chamber, a second portion comprising a plurality of first return fibers having a first end in communication with at least one spectrometer and a second end positioned to receive optical signals originating the processing chamber, and a third portion comprising a plurality of inactive fibers, wherein the second portion and the third portion are arranged on a common radius, and each source fiber is separated along the common radius by either at least one of the return fibers, at least one of the inactive fibers, or both return and inactive fibers.

BRIEF DESCRIPTION OF THE DRAWINGS

So that the manner in which the above recited features can be understood in detail, a more particular description, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 4A is an isometric cross-sectional view of one embodiment of a fiber optic cable bundle.

FIG. 4B is a cross-sectional view of another embodiment of a fiber optic cable bundle.

FIG. 5 is a schematic cross-sectional view of one embodiment of an optical transmission device.

To facilitate understanding, identical reference numerals have been used, wherever possible, to designate identical elements that are common to the figures. It is contemplated that elements of one embodiment may be advantageously utilized in other embodiments without further recitation.

DETAILED DESCRIPTION

While embodiments described herein are exemplarily described as an etch process performed in an etch chamber, it is contemplated that aspects described herein may be used in other chambers and processes. Examples include deposition chambers, such as epitaxial deposition chambers, chemical vapor deposition (CVD) chambers, plasma enhanced chemical vapor deposition (PECVD) chambers, physical vapor deposition (PVD) chambers, and the like. Other processes include plasma treating and rapid thermal processing (RTP) chambers, among other processes utilizing high temperatures and/or a need for real-time monitoring of process parameters.

Figure 1:
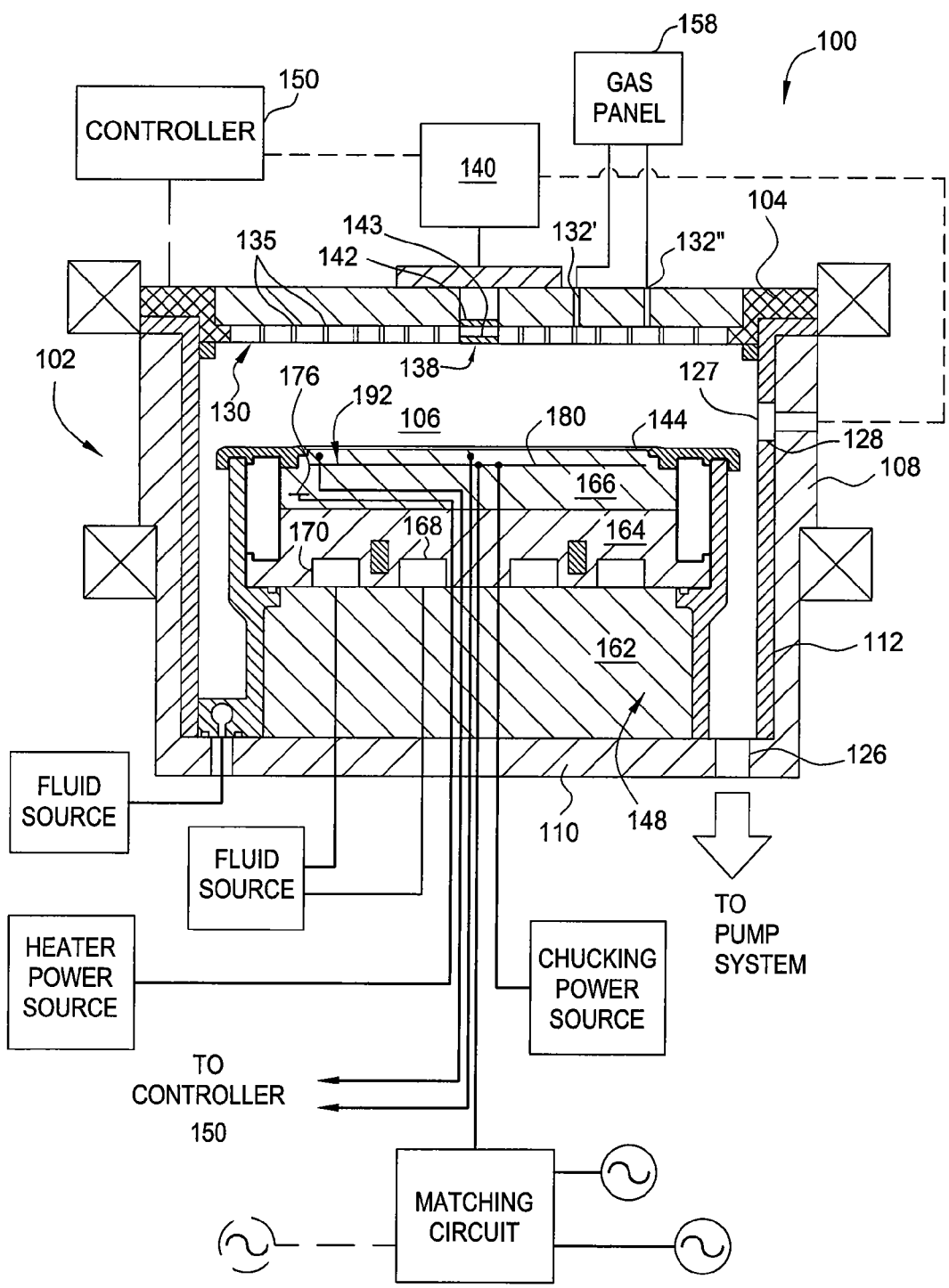
FIG. 1 is a sectional view of one embodiment of a processing chamber.

FIG. 1 is a sectional view of one embodiment of an exemplary processing chamber 100 adapted as a plasma chamber. In one embodiment, processing chamber 100 is suitable for etching high aspect ratio features in a substrate 144. The processing chamber 100 includes a chamber body 102 and a lid 104 which bounds a processing volume 106. The chamber body 102 is typically fabricated from aluminum, stainless steel, or other suitable material. The chamber body 102 generally includes sidewalls 108 and a bottom 110. A substrate access port (not shown) is generally defined in a side wall 108 and is selectively sealed by a slit valve to facilitate entry and egress of the substrate 144 from a substrate support assembly 148 disposed in the processing volume 106. An exhaust port 126 is defined in the chamber body 102 and couples the processing volume 106 to a pump system. The pump system generally includes one or more pumps and throttle valves utilized to evacuate and regulate the pressure of the processing volume 106 of the processing chamber 100. In one embodiment, the pump system maintains the pressure of the processing volume 106 at operating pressures typically between about 10 mTorr to about 20 Torr. A liner 112 may be coupled to an inner surface of sidewall 108 to protect the interior of the processing chamber 100. The liner 112 may also be disposed on portions of the substrate support assembly 148.

The substrate support assembly 148 is disposed in the processing volume 106 of the processing chamber 100 below the showerhead assembly 130 and holds the substrate 144 during processing. The plane of the substrate receiving surface of the substrate support assembly 148 is substantially parallel to the plane of the showerhead assembly 130. The substrate support assembly 148 generally includes a plurality of lift pins (not shown) disposed therethrough that are configured to lift the substrate from the support assembly 148 and facilitate exchange of the substrate 144 with a robot (not shown) in a conventional manner.

A controller 150 is coupled to the processing chamber 100. The controller 150 includes a central processing unit (CPU), a plurality of input/output (I/O) devices, support circuits (e.g., power supplies, clock circuits, bus controllers, cache, and the like), read-only memory (ROM), and random access memory (RAM). Instructions for an etch process, described below, may be stored on a computer readable medium within the controller 150 and executed by the controller 150.

In one embodiment, the substrate support assembly 148 includes a mounting plate 162, a base 164 and an electrostatic chuck 166. The mounting plate 162 is coupled to the bottom 110 of the chamber body 102 includes passages for routing utilities, such as fluids, power lines and sensor leads, among other utilities, to the base 164 and chuck 166. At least one of the base 164 or chuck 166 may include at least one optional embedded heater 176 and a plurality of conduits to control the lateral temperature profile of the support assembly 148. In the embodiment depicted in FIG. 1, two conduits 168, 170 are disposed in the base 164, while a resistive heater 176 is disposed in the chuck 166. The conduits 168, 170 and heater 176 are utilized to control the temperature of the base 164, thereby heating and/or cooling the electrostatic chuck 166, thereby controlling, at least in part, the temperature of the substrate 144 disposed on the electrostatic chuck 166.

The lid 104 is sealingly supported on the sidewall 108 of the chamber body 102 and may be opened to allow access to the processing volume 106 of the processing chamber 100. The lid 104 includes a window 142 that facilitates optical process monitoring. In one embodiment, the window 142 is comprised of sapphire, quartz, or other suitable material that is transmissive to an optical signal utilized by the optical monitoring system 140.

The processing chamber 100 includes at least one optical metrology module, such as an optical monitoring system 140 and/or an optical monitoring device 128. Both of the optical monitoring system 140 and optical monitoring device 128 are positioned to view or access at least one or both of the processing volume 106 of the chamber body 102 and the substrate 144. In one application, the optical signals analyzed by the optical monitoring system 140 provides information that enables process adjustment to compensate for incoming pattern inconsistencies (such as critical dimensions (CD's), film thickness, width/dimensions of structures, and the like), provides process state monitoring (such as plasma monitoring, temperature monitoring, CD's, and the like), and/or end point detection, among other functions.

The optical monitoring device 128 also includes a window 127 that is positioned generally radially on the chamber body 102 with respect to the substrate support assembly 148 and may function as an optical emission spectrum (OES) monitor. The optical monitoring device 128 may be configured to monitor plasma state, the degree of chamber matching, and source(s) of chamber fault, among other optical attributes within the processing chamber 100. One optical monitoring tool that may be adapted to benefit from embodiments described herein is the EyeD® full-spectrum, interferometric metrology module, available from Applied Materials, Inc., of Santa Clara, Calif. Thus, one or both of the optical monitoring system 140 and optical monitoring device 128 provide information relating to pattern inconsistencies, process state monitoring, and/or endpoint detection that may be monitored from vantage points positioned orthogonally and laterally with respect to the plane of the substrate 144.

The showerhead assembly 130 is coupled to an interior surface of the lid 104. The showerhead assembly 130 includes a plurality of apertures 135 that allow the gases flowing through the showerhead assembly 130 from an inlet port 132 into the processing volume 106 of the processing chamber 100 in a predefined distribution across the surface of the substrate 144 being processed in the chamber 100. The showerhead assembly 130 additionally includes a region transmissive to an optical metrology signal. The optically transmissive region or passage 138 in the showerhead assembly 130 is suitable for allowing the optical monitoring system 140 to view the processing volume 106 and/or substrate 144 positioned on the substrate support assembly 148. The passage 138 may be a material, an aperture or plurality of apertures formed or disposed in the showerhead assembly 130 that is substantially transmissive to the wavelengths of energy generated by, and reflected back to, the optical measuring system 140. The passage 138 is positioned substantially orthogonal to the plane of the substrate 144. In one embodiment, the passage 138 includes a plate 143 to protect the window 142 from the harsh environment of the processing volume 106. The plate 143 may be a sapphire material, a quartz material, an optical ceramic, such as yttrium oxide ($Y_2O_3$), or other suitable material. The plate 143 may alternatively be disposed in the lid 104 between the window 142 and the processing volume 106.

In one embodiment, the showerhead assembly 130 is configured with a plurality of zones that allow for separate control of gas flowing into the processing volume 106 of the processing chamber 100. In the embodiment FIG. 1, the showerhead assembly 130 has an inner zone and an outer zone that are separately coupled to a gas panel that is coupled to the processing chamber 100 to provide process and/or cleaning gases to the processing volume 106 through separate inlet ports 132', 132". The gas panel is coupled to gas sources (not shown) to deliver process gases and carrier gases to the inlet ports. Examples of processing gases include $SiCl_4$, HBr, $NF_3$, $O_2$ and $SiF_4$, among others. Examples of carrier gases include $N_2$, He, Ar, other gases inert to the process and non-reactive gases.

In one embodiment, the optical monitoring system 140 is capable of measuring CD's, film thickness, and plasma attributes either in-situ (during plasma processing) and/or ex-situ (before or after plasma processing). The optical monitoring system 140 may use one or more non-destructive optical measuring techniques, such as spectroscopy, interferometry, scatterometry, reflectometry, and the like. The optical monitoring system 140 may be, for example, configured to perform an interferometric monitoring technique (e.g., counting interference fringes in the time domain, measuring position of the fringes in the frequency domain, and the like) to measure the etch depth profile of the structure being formed on the substrate 144 in real time. Details of how to use optical monitoring for certain applications have been disclosed in commonly assigned U.S. application Ser. No. 10/674,568, filed on Sep. 29, 2003 and published as U.S. Patent Publication No. 2004/0203177 on Oct. 14, 2004, which is incorporated herein by reference.

Figure 2:
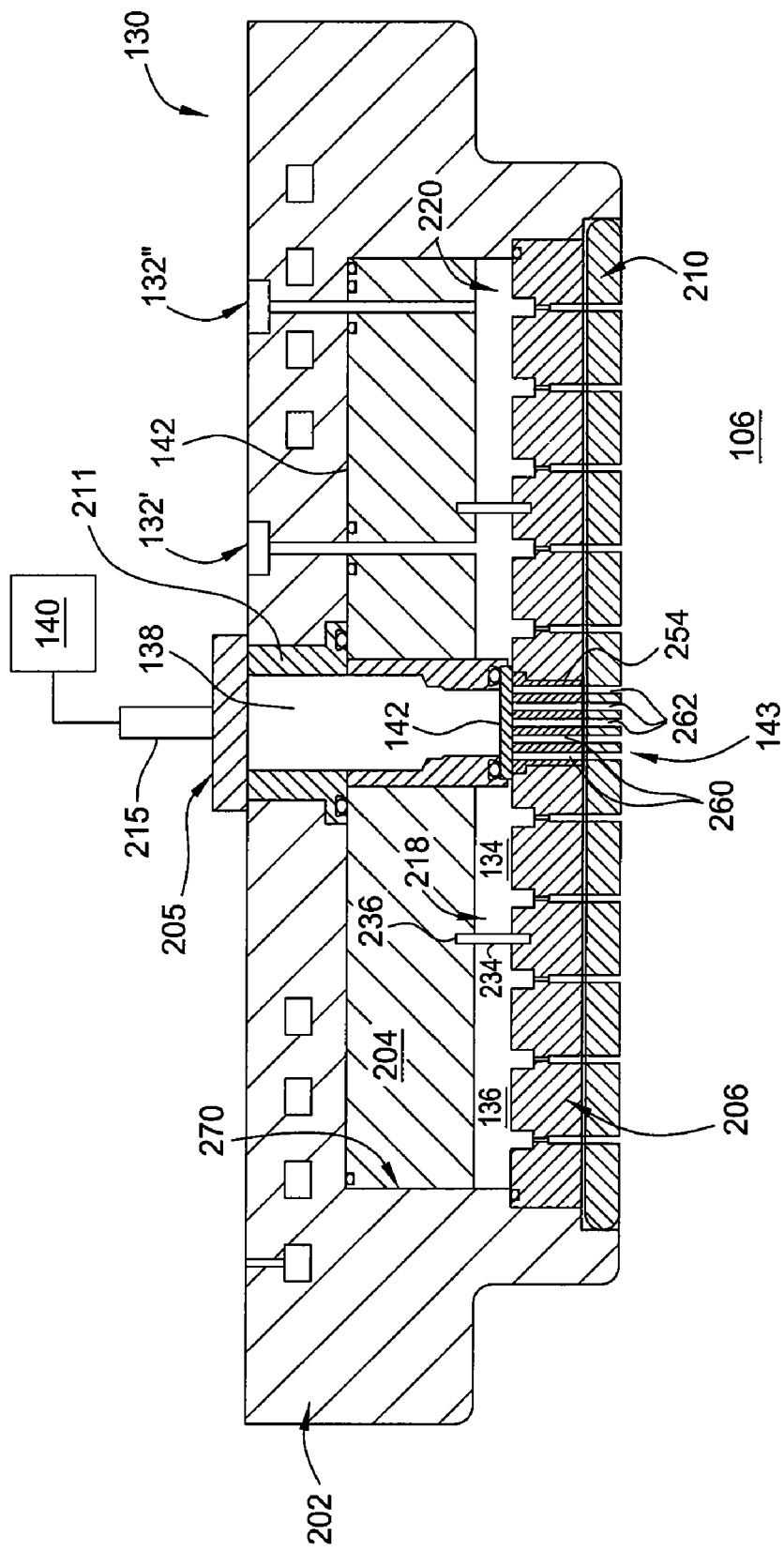
FIG. 2 is a sectional view of one embodiment of the showerhead assembly of FIG. 1.

FIG. 2 is a sectional view of one embodiment of the showerhead assembly 130. The showerhead assembly 130 generally includes a lid plate 202, upper plenum plate 204 and lower plenum plate 206, and a gas distribution plate 210. The upper and lower plenum plates 204, 206 are coupled together in a spaced-apart relation and disposed in a recess 270 formed in the lid plate 202 to define the upper structure of the showerhead assembly 130. An inner zone 134 defined between the plates 204, 206 is fluidly separated into at least two zones by a barrier 236. In the embodiment depicted in FIG. 2, the barrier 236 separates an inner plenum 218 from an outer plenum 220.

The passage 138 is formed through the showerhead assembly 130 to facilitate monitoring of chamber processes and/or substrate attributes by the optical monitoring system 140 and includes an optical transmission device 205. The passage 138 is generally located in a substantially geometric center of the showerhead assembly 130 and is defined by coaxially aligned apertures formed in the lid plate 202, the upper plenum plate 204, and the lower plenum plate 206. The passage 138 is generally formed at an angle substantially orthogonal to the plane of one or a combination of the lid plate 202, the upper plenum plate 204, the lower plenum plate 206, and the substrate 144 (not shown in this view).

In one embodiment, each of the coaxially aligned apertures in the lid plate 202 and plates 204, 206 are adapted to receive a lens device 211 and a plug 254, which are parts of the optical transmission device 205. In one embodiment, the lens device 211 is part of a collimator that is coupled to the optical monitoring system 140 by a fiber optic cable bundle 215.

The window 142 is sealingly disposed in the passage 138 to prevent gas leakage through the showerhead assembly 130 to the optical monitoring system 140. O-rings, not labeled with reference numerals in FIG. 2, are provided to seal the window 142 to the upper plenum plate 204 and the lid plate 202. Additional details of the lid plate 202 and the passage 138 formed through the lid plate 202, the upper plenum plate 204, and the lower plenum plate 206, as well as additional details of the processing chamber 100 of FIG. 1, may be found in U.S. patent application Ser. No. 11/381,523, filed May 3, 2006, which is incorporated by reference herein.

The plug 254 is configured to be transmissive to the signal utilized by the optical monitoring system 140. In one embodiment, the plug 254 includes a plurality of channels 260 which allow the optical monitoring system 140 to interface with the processing volume 106 of the chamber 100 while preventing plasma formation within the passages 260. In one embodiment, the channels 260 have an aspect ratio (height to diameter) of at least about 10:1, for example 14:1. In another embodiment, channels 260 have a diameter of less than or equal to the DEBYE length and/or the electron mean free path, for example less than about 1.5 mm, for example, about 0.9 mm. In another embodiment, channels 260 define an open area of up to about 60 percent open area. The plug 254 is generally fabricated from a material compatible with process chemistries. In one embodiment, the plug 254 is fabricated from a dielectric material, such as a ceramic. In another embodiment, the plug 254 is aluminum.

To extend the service life of the showerhead assembly 130, the gas distribution plate 210 is at least one of fabricated or coated with yttrium (Y) or an oxide thereof. In one embodiment, the gas distribution plate 210 is fabricated from bulk yttrium or oxide thereof to provide resistance to fluorinated chemistries. In other embodiments, the gas distribution plate 210 is fabricated from bulk yttrium oxide ($Y_2O_3$).

Optionally or additionally, the gas distribution plate 210 may include a plate 143 that is transmissive to an optical signal. The plate 143 may be coupled or fastened to the gas distribution plate 210 in the substantial geometric center of the gas distribution plate 210. In this embodiment, the plate 143 is made of yttrium or an oxide thereof, such as bulk $Y_2O_3$.

The channels 260 formed in the plug 254 are aligned with apertures 262 formed in the gas distribution plate 210. In applications where the plate 143 is used, apertures 262 are formed in the plate 143 to substantially align with channels 260 formed in the plug 254. The apertures 262 are clustered at the center of the gas distribution plate 210, and have a density, diameter (or width), profile, and open area suitable for facilitating the effective transmission of the optical signal through the gas distribution plate 210. In one embodiment, the number and sectional profile of the apertures 262 are similar to that of the channels 260. The window 142 makes the channels 260 and apertures 262 blind in a gas flow sense, while allowing optical transmission. Thus, the channels 260, apertures 262, and window 142 facilitate optical monitoring by the optical monitoring system 140 within the chamber 100 without vacuum loss or plasma damage to the structures defining the optical view path.

Figure 3:
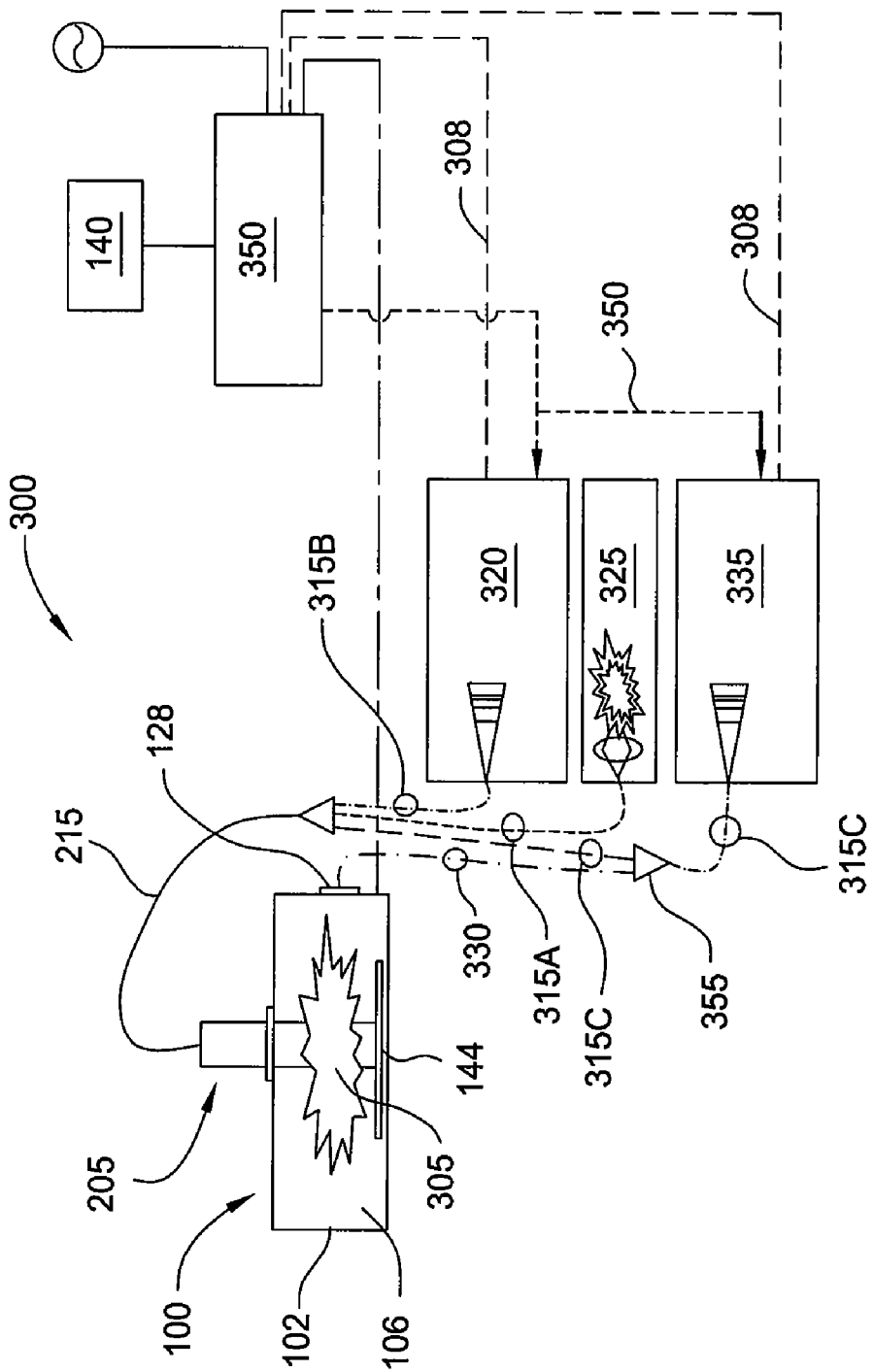
FIG. 3 is a schematic view of one embodiment of a spectral sensing system.

FIG. 3 is a schematic view of one embodiment of a spectral sensing system 300 that may be used with the processing chamber 100 of FIG. 1. The spectral sensing system 300 is coupled to the optical monitoring system 140 and the processing volume 106 of the chamber 100 by a fiber optic cable bundle 215 and an optical transmission device 205 that will be described with reference to FIG. 4. The spectral sensing system 300 includes a broadband light source 325 adapted to emit light having wavelengths in the ultra-violet visible (UV-Vis) range and near infra-red (NIR) range. In another embodiment, the broadband light source 325 emits light having wavelengths of about 200 nm to about 1800 nm. The broadband light source 325 may be a mercury lamp, a deuterium lamp, a xenon lamp, a halogen lamp, light emitting diodes (LEDs), or combinations thereof. The broadband light source 325 may further be adapted to be turned on and off and/or shuttered at a desired frequency, such as a strobe or flash. In one embodiment, the broadband light source 325 is a xenon (Xe) flash lamp adapted to emit light in wavelengths between about 200 nm to about 1800 nm.

The spectral sensing system 300 also includes at least two spectrometers 320, 335 that are adapted to receive optical energy from the processing volume 106. The spectrometers 320, 335 are configured to receive optical wavelengths in the UV-Vis and/or NIR wavelengths. In one embodiment, spectrometers 320, 335 are dual channel spectrometers with embedded controls. The spectrometer 320 may be configured to process optical signals in NIR wavelengths, while spectrometer 335 may be configured to process optical signals in UV-Vis wavelengths. In one application, spectrometer 320 is configured to process optical wavelengths between about 900 nm to about 1700 nm while spectrometer 335 is configured to process optical wavelengths between about 200 nm to about 800 nm. Each spectrometer 320, 335 is coupled to the controller 150, for example by Ethernet cables 308, which may be a local area network (LAN) cable, and other cabling applications. Additionally, line 350 may supply a signal from the controller 150 to one or both of spectrometers 320, 335 to synchronize magnetic fields in the spectrometers.

Various signal lines are shown schematically in FIG. 3 coupling the spectrometers 320, 335, and the optical monitoring device 128 and the optical transmission device 205. In this embodiment, signal lines, noted by reference numerals 315A-315C, represent one or more individual fibers of a fiber optic cable bundle 215. Broadband light from broadband light source 325 is transmitted to the processing volume 106 via line 315A to the optical transmission device 205 and impinges the substrate 144, which will be described in more detail in the description of FIG. 5. A portion of the optical energy reflected from the substrate 144 and/or plasma 305 is returned to one or both of the spectrometers 320, 335 by lines 315B and 315C. For example, optical wavelengths in between about 900 nm to 1700 nm are provided to spectrometer 320 and optical wavelengths between about 200 nm to about 800 nm are provided to spectrometer 335. The optical monitoring device 128 is coupled to a signal line 330 that is coupled to spectrometer 335 to provide a return signal from the chamber 100. The signal line 330 is coupled to line 315C by a connector 355. In one embodiment, the return signal is reflected energy from plasma 305 within the chamber 100. The signal line 330 may be a wire, a cable, or a fiber optic fiber.

As described above, spectrometer 335 is configured for OES measurements, which is indicative of the state of etching in the processing volume 106. For example, improved etch process control is facilitated by monitoring real-time transmission of the film on a photomask being etched. The absorbing layer of the mask (e.g., chromium (Cr)) has a small but measurable transmittance at the start of etching (typically 1% to 15%, depending on the film type), that increases in a predictable way as the film gets thinner during etching until it is gone completely (100% transmission), which may indicate the etch endpoint.

FIG. 4A is an isometric cross-sectional view of one embodiment of the fiber optic cable bundle 215. The fiber optic cable bundle 215 shown consists of 19 fibers, although more or less may be used, as needed. The size of individual fibers and number of fibers in the fiber optic bundle 215 are selected to minimize the size of the fiber optic cable bundle 215, which reduces the bulk of the fiber optic cable bundle 215. Referring again to FIG. 3, fibers 410 and 420 are collectively represented by line 315A and are used for transmitting optical signals from the broadband light source 325. Fibers 415 and 425 are represented by lines 315B and 315C, respectively, and are used for transmitting optical signals reflected from the substrate 144 and/or plasma 305. Fibers 405 are "dead" and may be used in alternative or additional optical transmission applications. In one embodiment, fibers 405 are used to add mechanical structure to the fiber optic cable bundle 215 and are referred to as structural fibers 405. In one embodiment, one or more of the fibers 405, 410, 415, 420, and 425 are multimode fibers.

FIG. 4B is a cross-sectional view of another embodiment of the fiber optic cable bundle 215. In this embodiment, each of the fibers 405, 410, 415, 420, and 425 are arranged in portions or zones and each of the portions or zones include at least one of the fibers. For example, zone 450 includes a single fiber (410), zone 455 includes 6 fibers (including 410, 415), and zone 460 includes 12 fibers (including 405, 420, 425). Additionally, fibers 410, 415, 420, and 425 are noted with an "S" or "R" for clarity, in which "S" denotes a source fiber, which delivers optical energy from the broadband light source 325 (FIG. 3) and "R" denotes a return fiber, which delivers optical energy from the processing volume 106 to spectrometers 320, 335 (FIG. 3).

The fibers $410_S$, $415_R$, $420_S$, and $425_R$ may be configured to provide selective attenuation of wavelengths. For example, fibers $410_S$ and $415_R$ are selected to attenuate green and blue wavelengths while transmitting infra red wavelengths preferentially while fibers $420_S$ and $425_R$ may be selected to preferentially transmit wavelengths in the UV-Vis range. Additionally, the pattern of fibers in zones 450, 455, and 460 minimizes or eliminates cross-talk between fibers. For example, fibers 410S, which supply NIR wavelengths to the processing volume 106, are positioned in the inner zone 450 and second zone 455, which provides a spatial separation from fibers $425_R$ in the outer zone 460. The spatial separation of the fibers 405, $410_S$, $415_R$, $420_S$, and $425_R$ facilitate preferential propagation of optical energy to minimize or eliminate residual cross-talk between fibers.

Each zone 450, 455, 460 may be arranged in a radial and/or coaxial relationship with each other, and may comprise a substantially circular geometry, which includes a substantially circular shape, a substantially hexagonal shape, and combinations thereof, among other polygonal shapes that may resemble a circle or hexagon. For example, zone 455 may be arranged radially outward from zone 450 in a substantially circular geometry. Likewise, zone 460 may be arranged radially outward from zone 455 in a substantially circular geometry.

In one embodiment, inner zone 450 is at a substantial geometric center of the fiber optic cable bundle 215, and the second and third zones 455, 460 are arranged concentrically about the inner zone 450. The second zone 455 includes a plurality of source lines (fibers 410S) and a plurality of return lines (fibers $415_R$) disposed in an alternative pattern where no source line is adjacent any return line. Outer zone 460 also includes a plurality of source lines (fibers $420_S$) and a plurality of return lines (fibers $425_R$) wherein one source fiber $420_S$ is positioned between two return fibers $425_R$. Additionally, each of the return fibers $425_R$ are separated by a structural fiber 405 in the outer zone 460.

FIG. 5 is a schematic cross-sectional view of one embodiment of an optical transmission device 205. The optical transmission device 205 is configured to be aligned in the passage 138 of FIGS. 1 and 2 and is adapted to transmit and receive optical signals from the optical monitoring system 140 via the fiber optic cable bundle 215. The optical transmission device 205 includes the fiber optic cable bundle 215, a lens device, such as a lens device 211, such as a collimator, which may include a mounting bracket 505 that is adapted to couple to an upper surface of the lid plate 202, a window 142, and a plug 254. The lens device 211 is adapted to transmit optical energy from the optical monitoring system 140 to the fiber optic cable bundle 215, the window 142, through channels 260 in the plug 254, and apertures 262 disposed in the gas distribution plate 210 to form a beam 525 that is substantially normal (e.g., substantially orthogonal) relative to the plane of the upper surface of the substrate support 148 and substrate 144 disposed thereon. Likewise, all or a great portion of reflected optical energy is directed to the apertures 262 and channels 260, and ultimately through the fiber optic cable bundle 215 to the optical monitoring system 140.

Embodiments described herein provide optical metrics based on the optical absorption edge of silicon (Si), which generally occurs near that of the silicon band gap. Generally, as temperature increases, the silicon band gap decreases, which causes the absorption edge of silicon to move toward a lower optical energy or longer wavelength. As a reference, the silicon band gap at or near room temperature is about 1.12 eV, which corresponds to an optical energy of about 1.107 microns (μm), and at about 410° C., the silicon band gap falls to about 0.9 eV, which corresponds to an optical energy of about 1.291 μm. In other words, as the temperature of a silicon wafer is raised, the opacity of the silicon decreases, and the spectral sensing system 300 described herein monitors the inflection point, which may be defined as a transition between opacity and transparency, as a function of temperature along with intensity changes at individual wavelengths, to extract information from the silicon wafer.

Figure 6A:
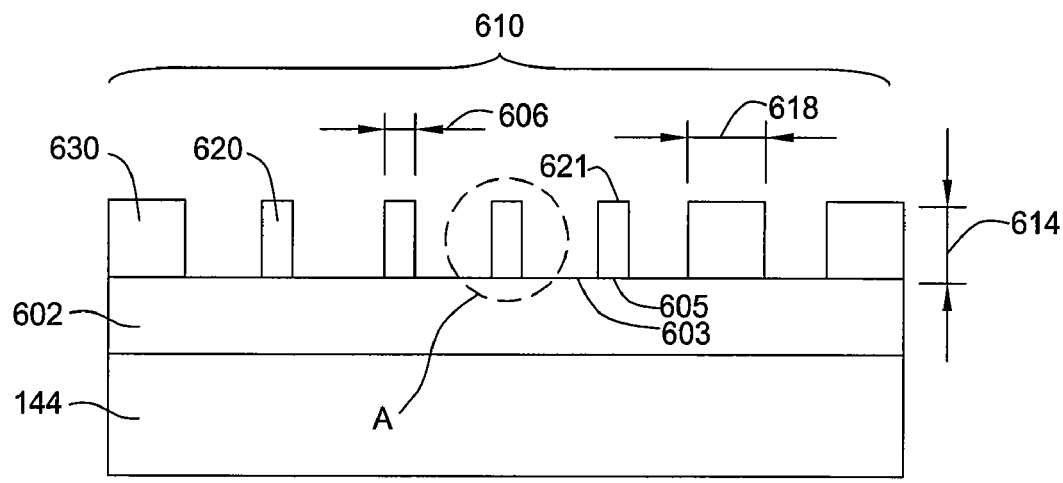
FIGS. 6A and 6B show schematic, cross-sectional views of a substrate in an etch process.
Figure 6B:
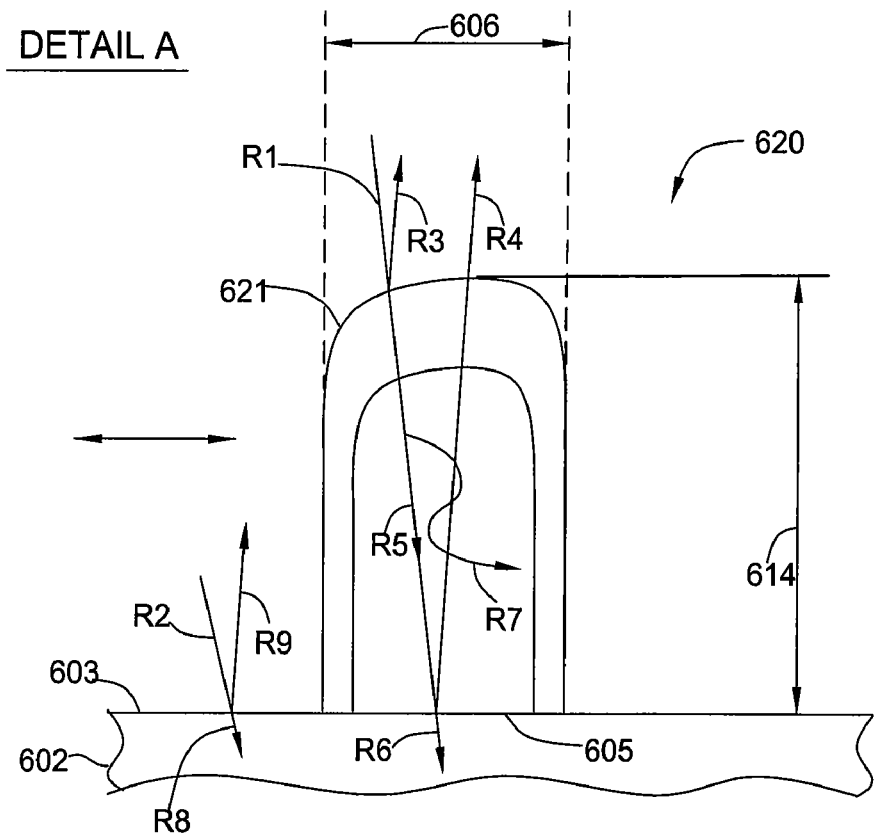

FIGS. 6A and 6B show schematic, cross-sectional views of a substrate 144 in an etch process. In FIG. 6A, a layer 602 and a patterned mask 610 are shown on the substrate 144. The layer 602 may comprise a single material film (e.g., dielectric film, metal film, or any other film used in integrated circuits) or a multi-layered film stack, either unpatterned (as shown) or, alternatively, patterned. During a subsequent etch process, the layer 602 may be etched using the patterned mask 610 as an etch mask. The layer 602 can be formed using any conventional thin film deposition technique, for example, atomic layer deposition (ALD), physical vapor deposition (PVD), chemical vapor deposition (CVD), plasma enhanced CVD (PECVD), and the like that is performed using, e.g., respective processing reactors of CENTURA®, ENDURA®, or other processing systems available from Applied Materials, Inc. of Santa Clara, Calif.

The patterned mask 610 may generally be in a form of a photoresist mask, an α-carbon (i.e., amorphous carbon) mask, a hard mask, an Advanced Patterning Film™ (APF) available from Applied Materials of Santa Clara, Calif., and the like. In one exemplary embodiment, the patterned mask 610 is a photoresist mask. Illustratively, referring to FIG. 6A, the patterned mask 610 has a height 614 and includes structures 620 and 630 (e.g., lines, walls, columns, and the like) having widths 606 and 618, respectively. The width 606 is smaller than the width 618 or a width of any other structure of the patterned mask 610.

In one embodiment, the spectral sensing system 300 is configured to measure in real time a metric that corresponds to a height 614 of structures 620 on the substrate 144 during an etch process. During the etch process, the optical transmission device 205 illuminates the substrate 144 using the broadband source 325 to produce incident radiation having wavelengths in UV-Vis and NIR ranges, e.g., from about 200 nm to about 1700 nm. Generally, such radiation is directed substantially perpendicular to the substrate 144 and illuminates a region on the substrate 144 of about 1 mm to about 12 mm, thus in one application, the a diametrical size of the beam is about 1 mm to about 12 mm. In one embodiment, the beam size illuminating the region on the substrate 144 is about 10 mm in diameter. In another embodiment, the beam size is less than or equal to 4 mm, such as about 1 mm, in diameter. More specifically, the optical transmission device 205 illuminates a region of the substrate 144 that is occupied by structures 620 having critical dimensions, such as the width 606.

To increase accuracy of the measurements, the intensity of incident radiation from the broadband light source 325 may optionally be modulated and/or pulsed, as well as polarized. In one embodiment, the frequency of modulation of the incident radiation may be up to about 10 Hz. Generally, the optical transmission device 205 may be configured to perform interferometric and/or spectrometric measurements as described above.

The incident radiation (ray R1), when radiated by the optical transmission device 205 to illuminate the structure 620, is partially reflected back (ray R3) from a surface 621 and partially propagates (ray R5) into the structure 620. The ray R5 further partially propagates through a surface 605 beneath the structure 620 into the layer 602 (ray R6) and absorbed therein. A portion of ray R5 is absorbed (ray R7) by the material of the structure 620 (e.g., photoresist), and a portion of ray R5 is reflected back (ray R4). Additionally, a portion of the incident radiation (ray R2) illuminating regions 603 near the structures 620 may partially propagate into layer 602 (ray R8) where ray R2 may be absorbed, with a portion reflected back (ray R9) from the layer 602.

Figure 7:
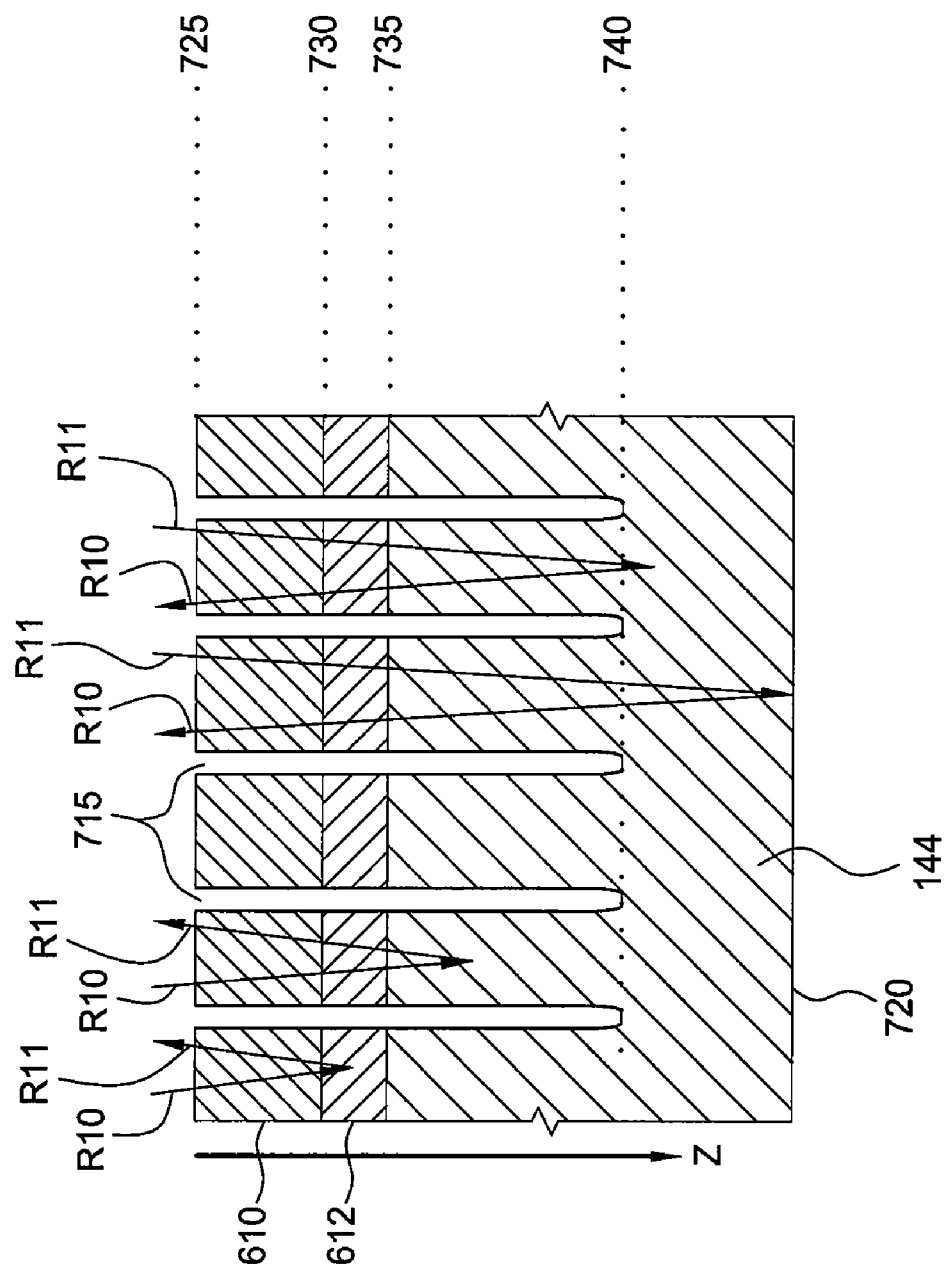
FIG. 7 is a schematic cross-sectional view of another embodiment of a substrate in an etch process

FIG. 7 is a schematic cross-sectional view of another embodiment of a substrate 144 in an etch process. In this embodiment, substrate 144 is silicon (Si) and trenches 715 are being etched in a vertical direction (direction Z) in the substrate 144 using a patterned mask 610 and a submask 612. Incident radiation (rays R10) from the optical transmission device 205 impinge the substrate 144 at different vertical depths and a portion of the rays are reflected back (rays R11) depending on the temperature of the substrate and/or the wavelength of optical energy from the optical transmission device 205. At some temperatures and/or wavelengths, ray R10 may be reflected from a backside 720 of the substrate 144 as shown in FIG. 7. The discontinuity in refractive indices of various layers, represented by reference numerals 725, 730, 735, and 740, generates clear interference fringe(s). The interference fringe(s) data is used to calculate etch depth based on Fourier analysis techniques based on frequency, or other analysis technique in the time domain.

Figure 8:
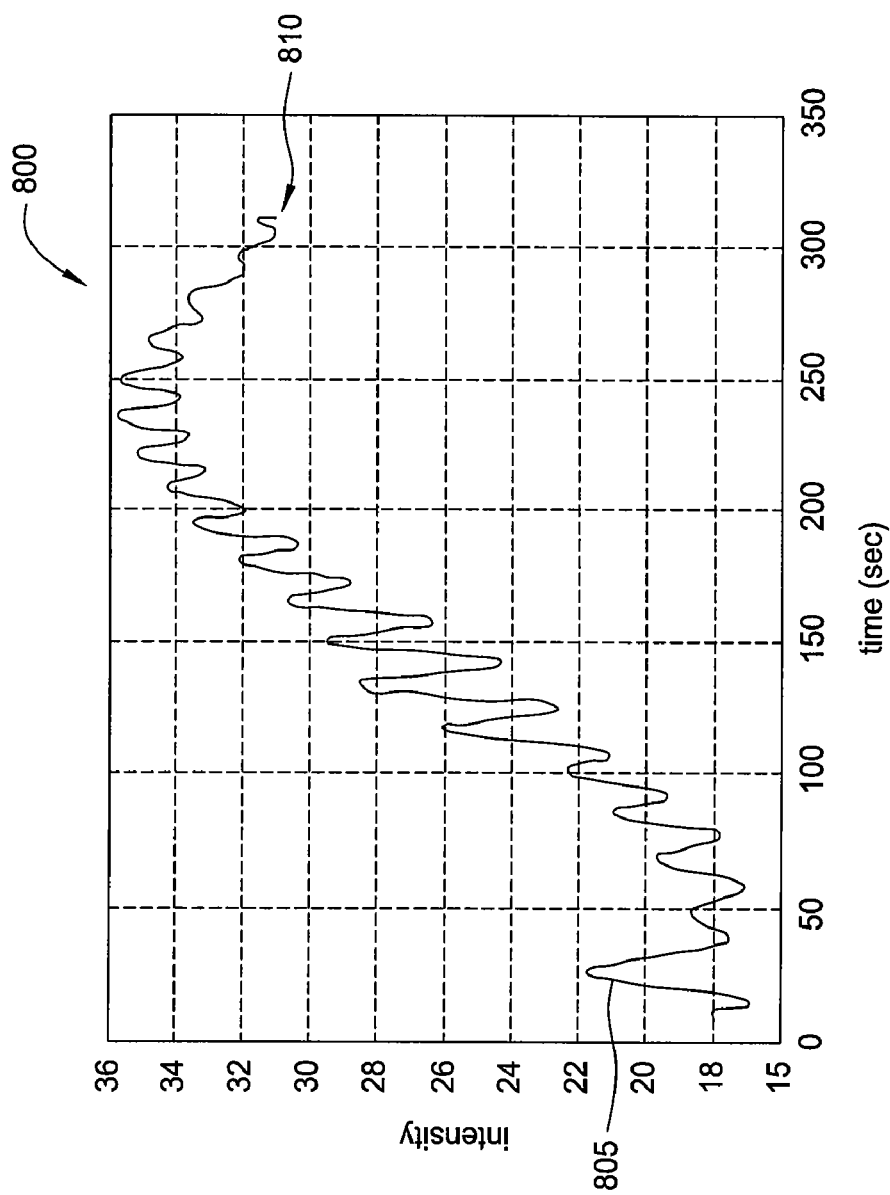
FIG. 8 is a graph representing data collected during a micro electromechanical system (MEMS) etch process.
Figure 9:
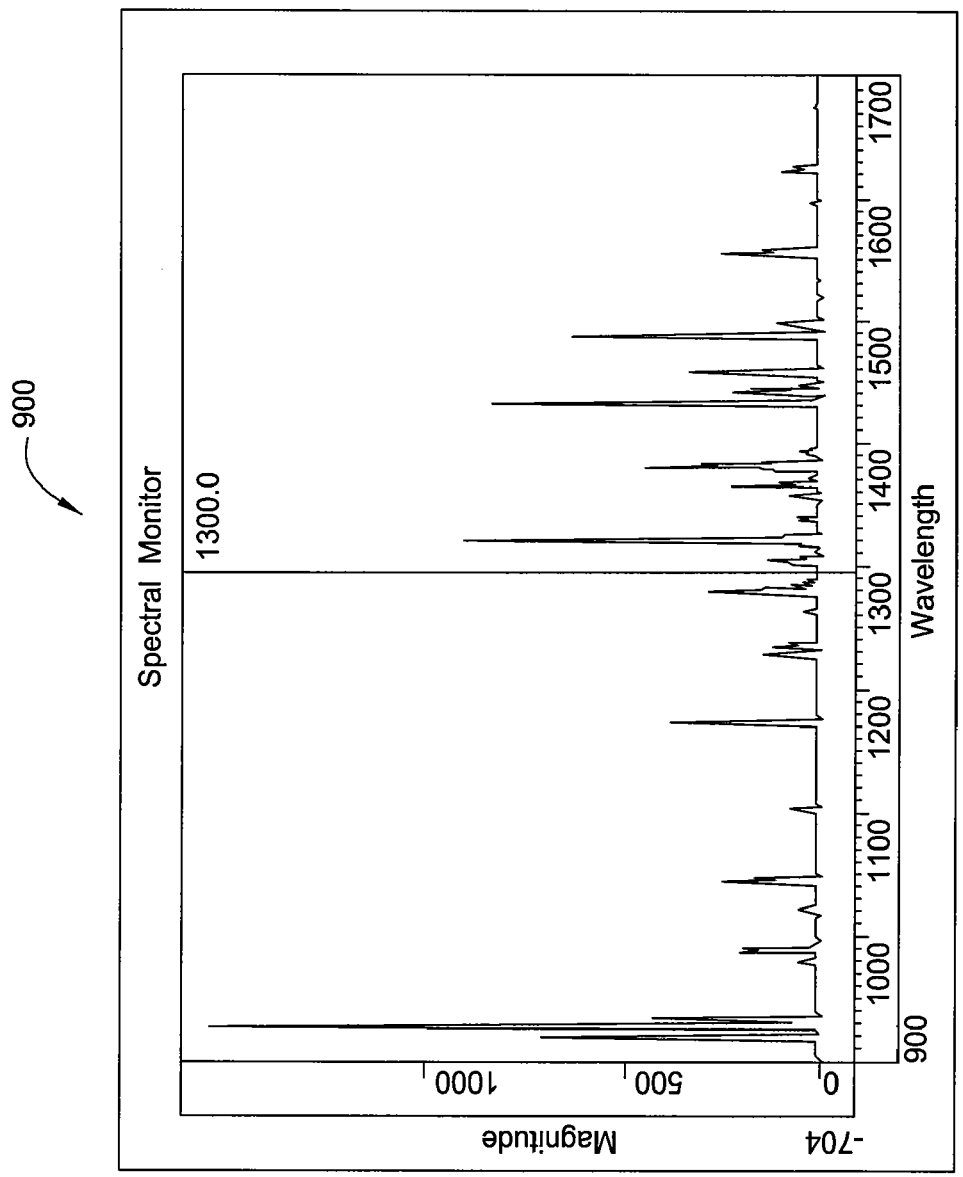
FIG. 9 is a graph showing plasma emission data collected during an etch process.

FIG. 8 is a graph 800 representing data collected during a micro electromechanical system (MEMS) etch process at a wavelength of 1.6 µm. The line 805 represents an interference signal collected during the etch process. Point 810 indicates a trench depth of about 4.39 µm based on the data shown in FIG. 8. FIG. 9 is a graph 900 showing plasma emission data collected during an etch process by the spectrometer 320 (FIG. 3) using NIR signals from the chamber 100.

Figure 10:
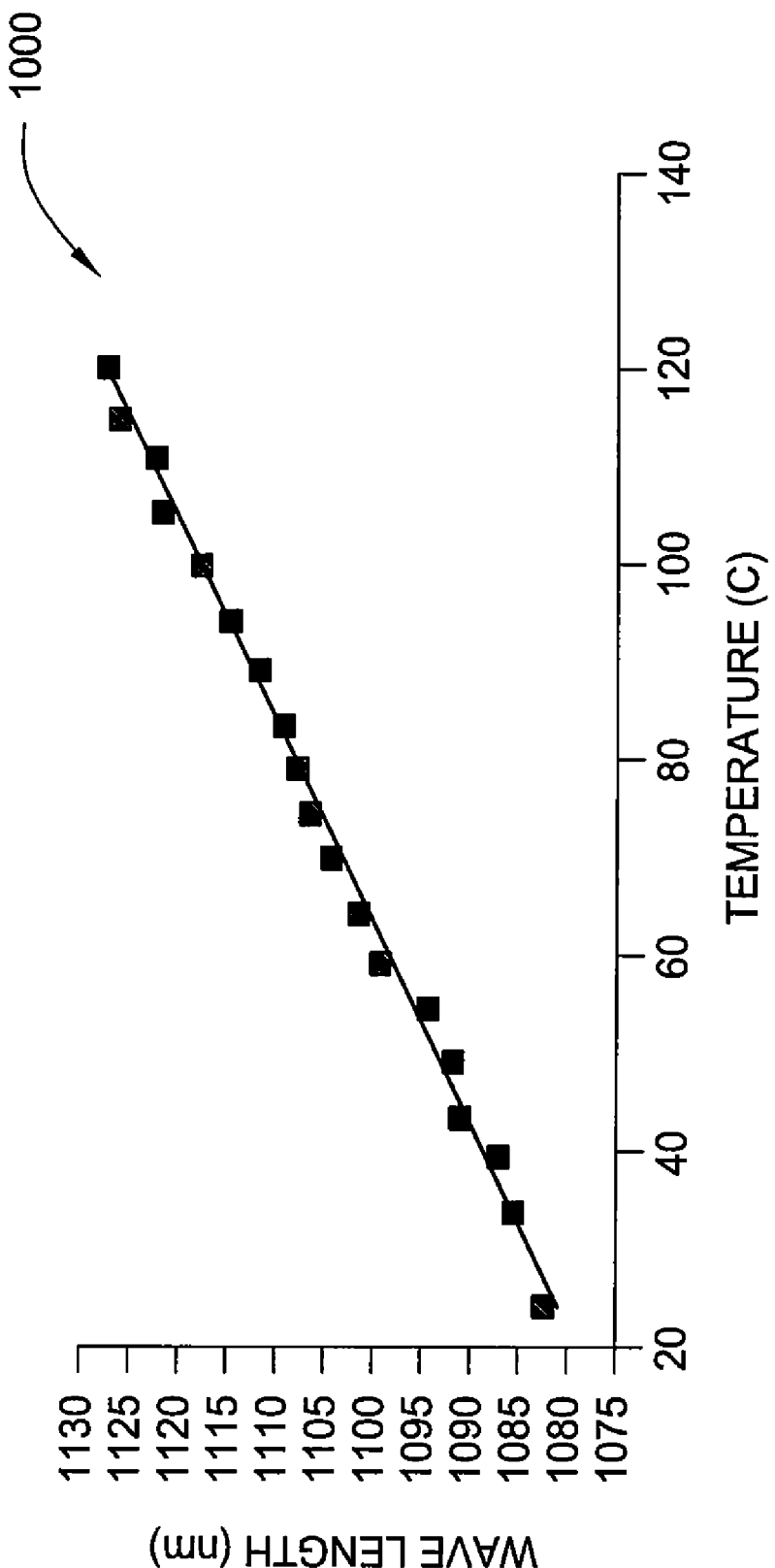
FIG. 10 is a graph showing points of the silicon absorption edge as a function of substrate temperature.

FIG. 10 is a graph 1000 showing points of the silicon absorption edge as a function of substrate temperature. It has been discovered in using the optical transmission device 205 that a spectral resolution of about 4 nm provides temperature measurement accuracy within about 2° C.

Calculation of Relative Absorption Spectrum

Figure 11:
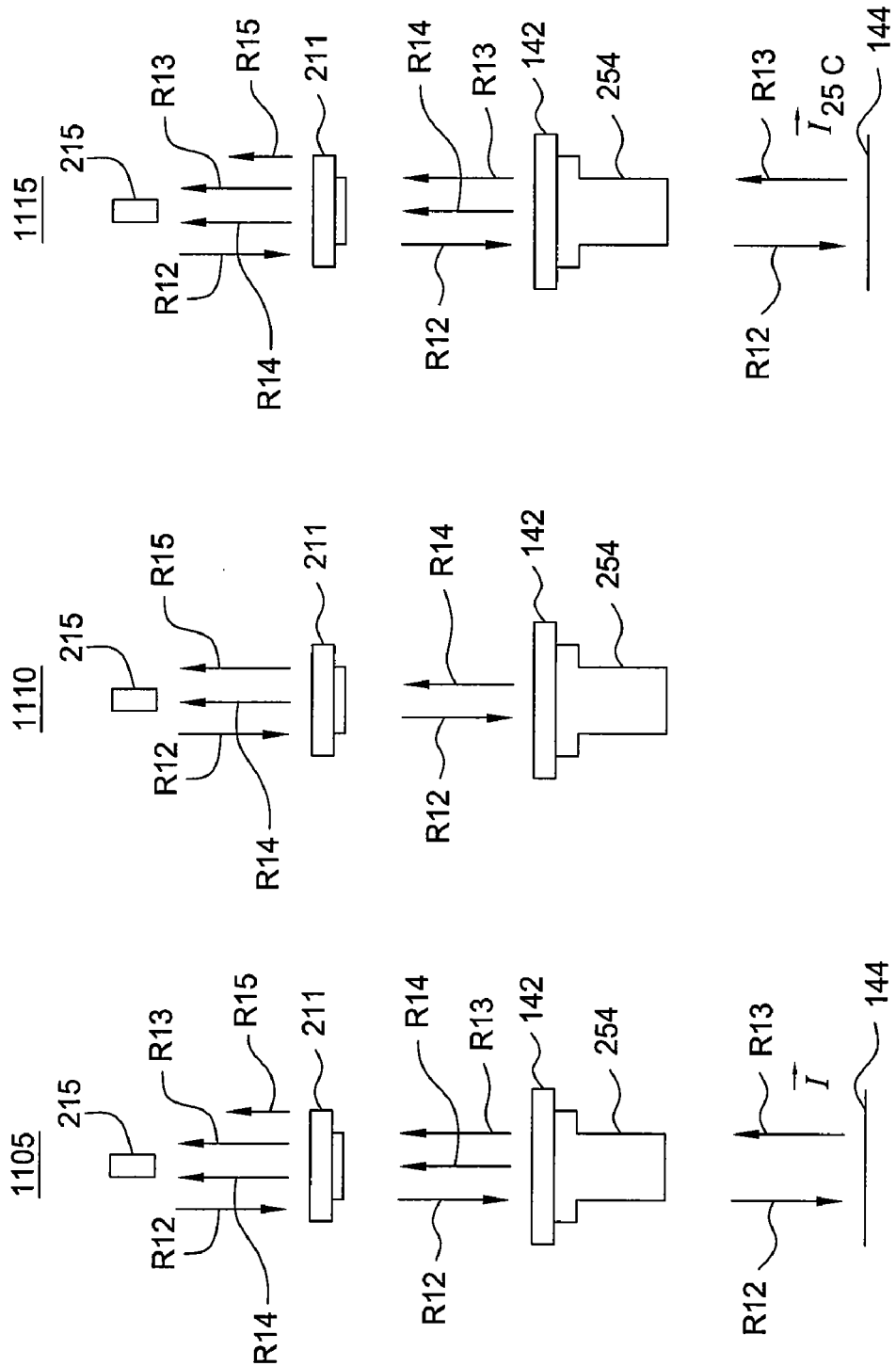
FIG. 11 is a schematic diagram showing reflectance of various elements of the optical transmission device.

FIG. 11 is a schematic diagram showing reflectance of various elements of the optical transmission device 205, such as the lens device 211, the window 142, and the plug 254 that may interfere with optical energy applied to the substrate 144. In order to compensate for the inadvertent reflectance, a determination of the relative absorption spectrum is provided. In the schematic labeled 1115, the fiber optic cable bundle 215 provides light indicated as ray R12 that passes through the lens device 211, the window 142, and the plug 254 to the surface of the substrate 144 maintained at a known temperature (such as at about 25° C.). The light is reflected off the substrate 144 through the plug 254, the window 142, and the lens device 211 to the fiber optic cable bundle 215. The reflected light, indicated by ray R13, is indicative of the temperature of the substrate, which includes error introduced by the light reflecting from system hardware, such as the plug 254, the window 142, and the lens device 211.

In order to account for this error, as shown in the schematic 1110, light is provided through the plug 254, the window 142, and the lens device 211, as indicated by ray R12, without a substrate within the chamber. A light absorbing disk may be disposed in the substrate support to prevent light from reflecting back to the source through the plug 254, the window 142, and the lens device 211. Thus, light reflected back to the fiber optic cable bundle 215 is reflected predominantly, if not solely, from the plug 254 and/or the window 142 (ray R14), and/or the lens device 211 (ray R15).

By using the information obtained from the reference substrate at schematic 1115 and the reflection error from schematic 1110, the temperature of a substrate 144 may be resolved as shown in schematic 1105 and calculated. The fiber optic cable bundle 215 provides light indicated by ray R12 that passes through the lens device 211, the window 142, and the plug 254 to the surface of the substrate 144 whose temperature is to be determined. The light is reflected off the substrate 144 through the plug 254, the window 142, and the lens device 211 to the fiber optic cable bundle 215, as indicated by ray R13. The reflected light R13 includes light reflected from substrate 144 (ray R13), the plug 254 and/or the window 142 (ray R14), and the lens device 211 (ray R 15). Using the information acquired through the techniques set forth at schematics 1110, 1115, the relative light absorption of the substrate 144 may be calculated by factoring out light reflected from the plug 254, the window 142, and the lens device 211, and calculating the light reflected from a substrate at a known temperature. A correction factor for lamp output differences may also be included in the calculation.

Elimination of Plasma Emission Effect

During the etch process, noise from plasma emissions may be sensed by the spectrometers 320, 335 and may provide inaccurate information. Therefore, it is desirable to reduce or eliminate the plasma emissions by filtering the plasma noise to provide more accurate optical information to the spectrometers.

Figure 12:
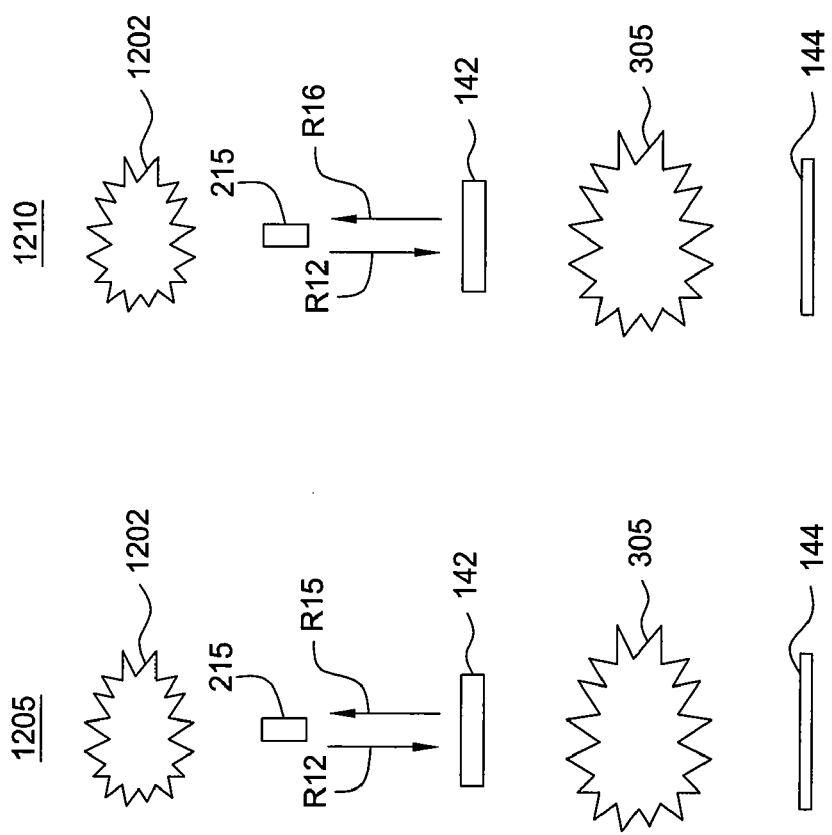
FIG. 12 is a schematic diagram depicting one embodiment of a plasma filtering method.

FIG. 12 is a schematic diagram depicting one embodiment of a plasma filtering method utilizing the broadband light source 325. In this embodiment, the broadband light source is a lamp 1202, such as a xenon flash lamp. Column 1205 indicates the lamp 1202 is "on" and ray R12 is directed toward the substrate 144. Ray R15 indicates returning radiation that may be reflected from the substrate 144 and hardware, plus radiation from the plasma 305. Column 1210 indicates the lamp 1202 is "off" and ray R16 indicates radiation from the plasma 305. The intensity "I" of ray R15 and ray R16 may be determined, and the reflectance spectrum of the hardware and lamp may be calculated by the following equation:

$$I_{lamp\ on} - I_{lamp\ off}$$

In another embodiment, the plasma emission effect may be filtered using a median spectral filter. In this embodiment, the following algorithm is used:

$$A_i = \text{Median}(A_{i-n/2}, A_{i-n/2+1}, \ldots A_{i+n/2-1}, A_{i+n/2})$$

wherein: i=intensity, and n=number of substrates.

Figure 13:
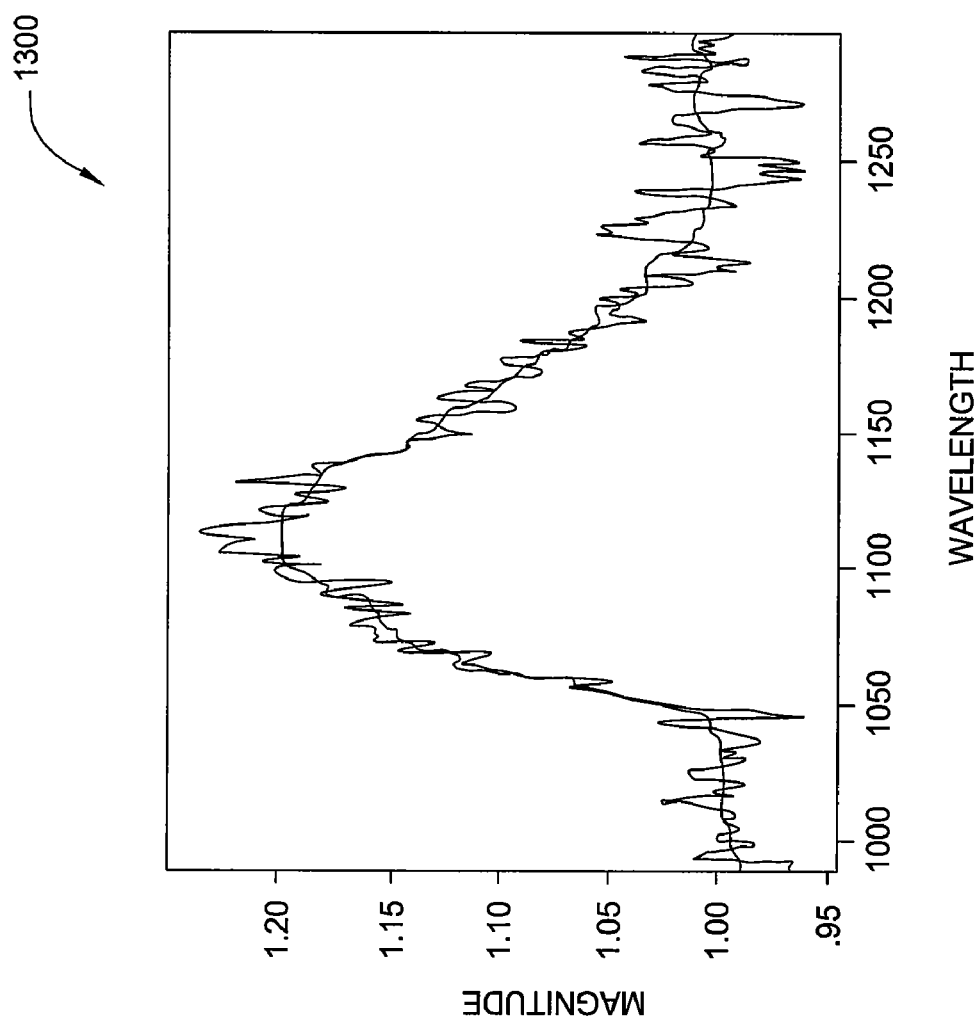
FIG. 13 is a graph showing raw absorption spectrum data as compared to filtered absorption spectrum data.

FIG. 13 is a graph 1300 showing raw absorption spectrum data as compared to filtered absorption spectrum data. Unfiltered absorption spectrum data is indicated by trace 1305 and filtered absorption spectrum data is indicated by trace 1310. As shown, intensity spikes from plasma emissions are substantially eliminated.

In operation, a substrate 144 is provided to a processing chamber configured as described above, and disposed on a substrate support. An etchant gas is provided to the processing chamber and ignited into a plasma. A fiber optic cable bundle 215 directed to an optically transmissive region of the upper portion of the processing chamber carries electromagnetic energy of at least one frequency or frequency range, into the processing chamber. The bundle may contain, for example, a first active bundle comprising a first source bundle for carrying electromagnetic energy of a first frequency to the processing chamber, and a first receiving bundle for detecting electromagnetic energy of the first frequency inside the processing chamber. The bundle may also contain a second source bundle and second receiving bundle for carrying a second frequency. The fiber optic cable bundle may also comprise a spacing bundle, which may be a third bundle, adapted to minimize interference among signals propagating through the other active bundles. A structural bundle may also be adapted to promote rigidity or mechanical strength within the fiber optic cable bundle.

The fiber optic cable bundle 215 directs the energy toward the substrate in a manner generally orthogonal to a surface of the substrate. The energy provided to the fiber optic cable bundle may be generated at one or more specific frequencies, or may be a broadband spectrum energy. At least a portion of the incident energy is reflected from the substrate back to the fiber optic bundle and is carried by the bundle to one or more spectral analyzers. The spectral analyzers compare the spectral characteristics of the reflected energy to that of the incident energy to determine the status of the substrate, such as progress of the etching process and/or temperature. Process conditions are adjusted based on the analysis of the reflected energy.

Figure 14:
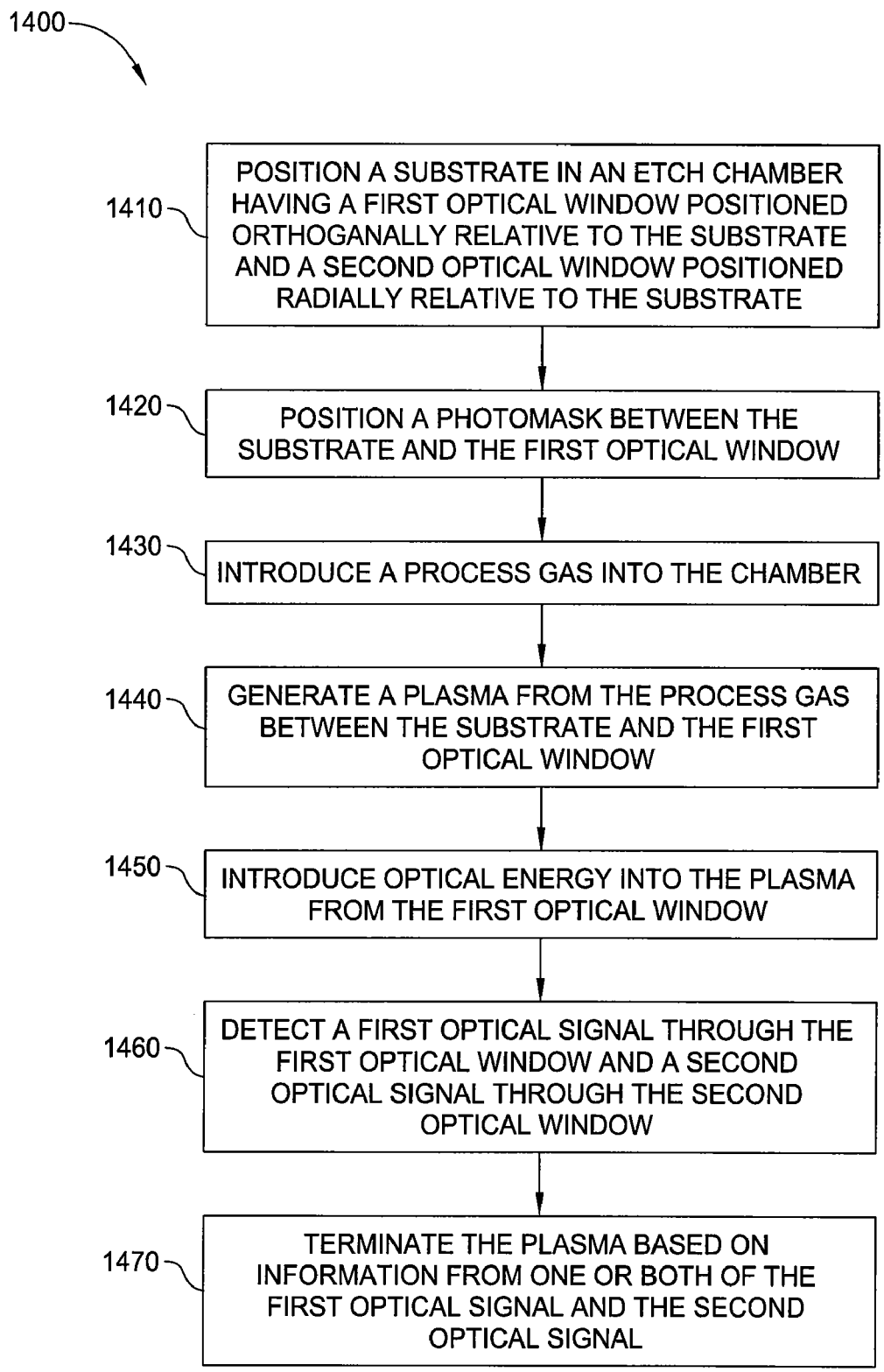
FIG. 14 is a flowchart showing one embodiment of an endpoint detection method.

FIG. 14 is a flowchart showing one embodiment of an endpoint detection method 1400. At 1410, a substrate is provided to a chamber 100 and positioned on the substrate support. The chamber 100 includes a first optical window, such as window 142, which is positioned normal to the plane of the substrate and/or substrate support, and a second window, such as window 127, which is positioned in a general radial direction with respect to the substrate and/or substrate support. At 1420, a photomask, such as patterned mask 610, is positioned adjacent the substrate to facilitate pattern formation on the substrate. A process gas is introduced into the chamber at 1430 and a plasma of process gas is generated between the substrate and the first optical window (142) at 1440. At 1450, optical energy, such as light in the UV-Vis and/or NIR spectrum is directed into the plasma toward the substrate. During processing, a first signal, such as reflected light from the substrate, is detected at the first window, and a second signal, such as a signal indicative of plasma attributes, is detected at the second window (127) as shown at 1460. In one embodiment, the first signal includes IEP metrics and the second signal includes OES metrics. Based on one or both of the IEP and OES metrics detected at windows 142 and/or 127, the plasma generated at 1440 is terminated, as shown at 1470. For example, IEP metrics may include attributes such as trench depth, trench width, as well as other attributes and metrics indicating the etch progression, as well as temperature indications. OES metrics include plasma state indications as well as etch progression, among others. Additionally, prior to termination of the plasma, temperature of the substrate may be monitored and/or adjusted based on information detected at the first window.

Embodiments described herein are directed to IEP and OES analyses using a broadband energy source, such as a broadband light source 325 and/or a lamp 1202 as described herein. One or both of these analyses may be used to determine an end point of the etch process, temperature of the substrate, or etch selectivity, among other parameters, and process conditions may be adjusted based on one or both of the analyses. Thus, electromagnetic energy emitted by the plasma may be detected by an optical detector disposed in a side wall of the chamber in a radial relationship to the substrate, and electromagnetic energy and/or light in a known frequency may be detected with an optical detector disposed at an angle substantially normal to the substrate. Energy emitted by the plasma and/or light at known frequencies may be analyzed and compared to the other analyses described above to improve the accuracy of the result.

Embodiments described herein provide processing benefits including confirmation of reaching both OES endpoint and IEP endpoint for greater reliability, especially for low open area trench processes. For example, OES and IEP endpoint may be used to detect process drift and/or inaccuracies in one of the endpoint methods by comparison of the two methods. Process uniformity evaluation and monitoring to center-fast or center-slow etch conditions may be improved by comparing endpoint times for the IEP and OES endpoint (average). Normalization the OES signal through a photomask by dividing the IEP signal by the OES signal. This normalization provides for a true transmission measurement, largely independent of plasma brightness and fluctuations and also allows for a comparison between the measured spectral transmission of the photomask and a real-time model for the transmission, thereby allowing determination of the etching layer thickness (e.g., a Cr layer) during etch. The normalization also allows for a comparison between the measured spectral transmission of the photomask and a real-time model for the spectral transmission, thereby allowing determination of the masking layer thickness (e.g., photoresist) during etch.

While the foregoing is directed to embodiments of the present invention, other and further embodiments of the invention may be devised without departing from the basic scope thereof, and the scope thereof is determined by the claims that follow.

What is claimed is:

1. A processing chamber comprising:
a chamber body assembly having a processing volume;
a showerhead assembly coupled to a ceiling of the chamber body and having a region transmissive to an optical metrology signal;
an optical monitoring device arranged to view the processing volume at a radial position of the chamber body; and
a spectral sensing system comprising a fiber optic bundle arranged to view the processing volume of the chamber body through the transmissive region of the showerhead assembly at an angle orthogonal to the plane of the showerhead, wherein the fiber optic bundle further comprises:
a first active portion comprising a plurality of first source fibers and a plurality of first signal fibers;
a second active portion comprising a plurality of second source fibers and a plurality of second signal fibers; and
a third inactive portion comprising a plurality of inactive fibers.

2. The processing chamber of claim 1, wherein a portion of the plurality of first source fibers are arranged in a spaced-apart relationship relative to the plurality of first signal fibers.

3. The processing chamber of claim 2, wherein the portion of the first plurality of first source fibers and the plurality of first signal fibers are arranged alternately in a substantially circular geometry.

4. The processing chamber of claim 1, wherein each of the plurality of second signal fibers are adjacent at least one of the plurality of first source fibers and at least one of the plurality of first signal fibers.

5. The processing chamber of claim 4, wherein the plurality of second signal fibers are arranged in a substantially circular geometry and one of the plurality of second source fibers therebetween.

6. The processing chamber of claim 1, wherein the plurality of second signal fibers and the plurality of inactive fibers are arranged in a substantially circular geometry.

7. The processing chamber of claim 6, wherein each of the plurality of second signal fibers are separated by one inactive fiber.

8. A fiber optic cable bundle coupled to a radiation source and at least one spectrometer, comprising:
a plurality of optical fibers secured in a bundle, the bundle comprising a first portion comprising at least one source fiber having a first end coupled to the radiation source and a second end positioned to direct radiation from the source into a processing chamber;
a second portion comprising a plurality of first return fibers having a first end in communication with the at least one spectrometer and a second end positioned to receive optical signals originating the processing chamber; and
a third portion comprising a plurality of inactive fibers, wherein the second portion and the third portion are arranged on a common radius, and each source fiber is separated along the common radius by either at least one of the return fibers, at least one of the inactive fibers, or both return and inactive fibers.

9. The fiber optic cable bundle of claim 8, wherein the first, second, and third portions are arranged alternately in a substantially circular geometry.

10. The fiber optic cable bundle of claim 8, wherein the second portion comprises a plurality of first source fibers and a plurality of first signal fibers, each of the plurality of second signal fibers are adjacent at least one of the plurality of first source fibers and at least one of the plurality of first signal fibers.

11. The fiber optic cable bundle of claim 10, wherein the plurality of second signal fibers are arranged in a substantially circular geometry and one of the plurality of second source fibers therebetween.

12. The fiber optic cable bundle of claim 8, wherein the third portion comprises a plurality of second signal fibers that are adjacent the plurality of inactive fibers in a substantially circular geometry.

13. The fiber optic cable bundle of claim 12, wherein each of the plurality of second signal fibers are separated by one inactive fiber.

14. The fiber optic cable bundle of claim 8, wherein the fiber optic cable further comprises a substantially circular geometry which includes the second portion located radially inward relative to the third portion, and the at least one source fiber is located radially inward relative to the second portion.

15. A method for processing a substrate, comprising:
etching a substrate positioned on a substrate support disposed in an etch chamber, the substrate etched through a patterned masking layer in the presence of a plasma;
introducing optical energy into the plasma and directed towards the substrate;
collecting a first signal and a second signal from the plasma;
routing the first signal through a fiber optic bundle to a detector, wherein the fiber optic cable bundle comprises:
a first portion comprising at least one source fiber having a first end coupled to a radiation source and a second end positioned to direct radiation from the source into a processing chamber;
a second portion comprising a plurality of first return fibers having a first end in communication with at least one spectrometer and a second end positioned to receive optical signals originating the processing chamber; and
a third portion comprising a plurality of inactive fibers, wherein the second portion and the third portion are arranged on a common radius, and each source fiber is separated along the common radius by either at least one of the return fibers, at least one of the inactive fibers, or both return and inactive fibers; and
controlling the etch process in response to the collected signals.

16. The method of claim 15, wherein the first signal is generated by optical energy reflected from the substrate.

17. The method of claim 15, wherein the second signal is generated by optical energy from the plasma.

18. The method of claim 15, further comprising:
intermittently collecting the first signal while etching the substrate.

19. The method of claim 15, wherein the optical energy is directed towards the substrate at an angle normal to the plane of the substrate.

20. The method of claim 15, wherein the optical energy is directed towards the substrate by the first portion of fibers.

21. The method of claim 20, wherein the optical energy is directed towards the substrate at an angle normal to the plane of the substrate.

22. The method of claim 15, wherein the first signal is collected by the second portion at an orthogonal angle relative to the plane of the substrate.

23. The method of claim 22, wherein the second signal is collected from a radial position relative to the substrate.

24. A computer-readable medium containing instructions, that when executed by a processing system, control an etch process performed in the processing system, the etch process comprising:
etching a substrate positioned on a substrate support disposed in a processing system, the substrate etched through a patterned masking layer in the presence of a plasma;
directing optical energy through the plasma towards the substrate;
collecting a first signal and a second signal from the plasma;
routing the first signal through a fiber optic bundle to a detector, wherein the fiber optic cable bundle comprises:

a first portion comprising at least one source fiber having a first end coupled to a radiation source and a second end positioned to direct radiation from the source into a processing chamber;

a second portion comprising a plurality of first return fibers having a first end in communication with at least one spectrometer and a second end positioned to receive optical signals originating the processing chamber; and a third portion comprising a plurality of inactive fibers, wherein the second portion and the third portion are arranged on a common radius, and each source fiber is separated along the common radius by either at least one of the return fibers, at least one of the inactive fibers, or both return and inactive fibers; and controlling the etch process in response to the collected signals.

* * * * *